(12) United States Patent
Eder

(10) Patent No.: US 6,260,425 B1
(45) Date of Patent: Jul. 17, 2001

(54) INSPECTION MACHINE FOR BOTTLES OR SIMILAR

(75) Inventor: Erich Eder, Donaustauf (DE)

(73) Assignee: Krones AG Hermann Kronseder Maschinenfabrik, Neutraubling (DE)

(*) Notice: Subject to any disclaimer, the term of this patent is extended or adjusted under 35 U.S.C. 154(b) by 0 days.

(21) Appl. No.: 09/125,277

(22) PCT Filed: Apr. 11, 1997

(86) PCT No.: PCT/EP97/06081

§ 371 Date: Oct. 27, 1999

§ 102(e) Date: Oct. 27, 1999

(87) PCT Pub. No.: WO99/23480

PCT Pub. Date: May 14, 1999

(51) Int. Cl.$^7$ .................. G01M 19/00; G01N 21/90
(52) U.S. Cl. ................... 73/865.8; 198/339.1; 356/239.4
(58) Field of Search .................... 73/865.8, 865.9; 198/339.1; 250/223 B; 356/240.1, 239.2, 239.5

(56) References Cited

U.S. PATENT DOCUMENTS

| 4,852,415 | * | 8/1989 | Bogatzki et al. ............... 73/865.8 |
| 5,546,819 | * | 8/1996 | Zodrow ......................... 73/865.8 |
| 5,608,516 | * | 3/1997 | Emery ....................... 250/223 B X |
| 6,012,344 | * | 1/2000 | Holbo ............................ 73/865.8 |
| 6,116,404 | * | 9/2000 | Heuft et al. ................. 198/339.1 |

FOREIGN PATENT DOCUMENTS

| 3320476 C1 | * | 8/1984 | (DE) . |
| 19605133 A1 | * | 8/1997 | (DE) . |
| 124164 A1 | * | 11/1984 | (EP) . |
| 415 154 A1 | * | 3/1991 | (EP) ........................ 209/524 |
| 487 402 A1 | * | 5/1992 | (EP) ........................ 356/426 |
| 2182434 | * | 5/1987 | (GB) . |
| 97/30343 | * | 8/1997 | (WO) . |

* cited by examiner

Primary Examiner—Thomas P. Noland
(74) Attorney, Agent, or Firm—Marshall, O'Toole, Gerstein, Murray & Borun

(57) ABSTRACT

On an inspection machine for bottles or the like with an inward conveyor and arranged thereon a first lateral inspection device, with an outward conveyor and arranged thereon a second lateral inspection device, and with an intermediate conveyor which spans a gap between the latter and arranged thereon a base inspection device, the inward conveyor and the outward conveyor are arranged at an angle with respect to one another, whereas the intermediate conveyor incorporating two endless conveyor mechanisms adapted to be driven at the same speed extends at least partly in an arc. This enables the two lateral inspection devices to check different peripheral zones of the bottles without the bottles rotating independently and the malfunctions thereby caused, so as to achieve a high level of inspection accuracy.

9 Claims, 1 Drawing Sheet

INSPECTION MACHINE FOR BOTTLES OR SIMILAR

FIELD OF THE INVENTION

The invention relates-to-an inspection machine for bottles or the like, particularly as utilizing conveyors.

BACKGROUND OF THE INVENTION

One such inspection machine is already in use, on which a rotary conveyor operating with a driven endless conveying mechanism and a facing stationary friction surface is arranged on the inward conveyor some distance ahead of the intermediate conveyor, within the operating range of the single lateral inspection device. This known inspection machine, which is compact in its construction, makes it possible for bottles or the like to be checked for dirt, flaws, etc. both in the base area and in the side wall area. The bottles are transferred in a secure upright position to the onward conveyor by the conveying mechanisms of the intermediate conveyor, which are being driven at the same speed. However, it is a drawback that the rotary conveyor is only able to act on the bottles in their lowermost wall area, so as not to overly restrict the field of view of the lateral inspection device. Since, moreover, a large angle of rotation is required over a relatively short transfer distance, the transportation of the bottles in the region of the rotary conveyor is extremely unstable and the results of the inspection fail to meet the standard required. Besides, it is very easy for the bottles to fall over before they are intercepted by the intermediate conveyor once they have negotiated the rotary conveyor. The known inspection machine is therefore unsuitable for high throughput levels.

Also in use is an inspection machine having an inward conveyor, an outward conveyor arranged at a distance therefrom and an intermediate conveyor which transfers rotationally symmetrical bottles between the inward and outward conveyors. On this inspection machine a first lateral inspection device is arranged on the inward conveyor, a second lateral inspection device on the outward conveyor and a base inspection device in the area of the gap between the inward and the outward conveyors. The intermediate conveyor features two endless conveyor mechanisms which act on opposite sides of the bottles and are driven at different speeds, and which turn the bottles through a certain angle on their way from the inward conveyor to the outward conveyor. The bottles are therefore turning as the intermediate conveyor hands them over to the outward conveyor, and they can easily be set spinning and topple over. This results in damage to the second lateral inspection device and serious disruptions to production. Furthermore, the fact that the bottles are independently rotating in the region of the base inspection device can disrupt the operation of the latter.

SUMMARY OF THE INVENTION

It is the object of the invention to improve the inspection machine of the type indicated at the beginning in terms of the efficiency and operational reliability of the bottle transportation process and in terms of the accuracy of inspection in the side wall area.

On an inspection machine in accordance with the invention the bottles are transported as it were parallel to themselves in the arcuate section of the intermediate conveyor without being rotated about their spatial median axis, with the result that there is now absolutely no potential for malfunctioning due to independent rotation on the part of the bottles. In spite of this, the angled arrangement of the inward conveyor and the outward conveyor means that the bottles adopt a position thereon at a different angle, with the result that the two lateral inspection devices are able to observe different peripheral zones of the bottles.

Practical refinements of the invention which all contribute to making the transportation of the containers particularly stable, are contained in the subsidiary claims.

Particularly noteworthy are the refinements of the present invention, which result in a difference in the angular position of the bottles on the inward conveyor, on the one hand, and on the outward conveyor, on the other, by approx. 90 degrees, which is optimal for the accuracy of the side wall inspection.

BRIEF DESCRIPTION OF THE DRAWINGS

One example of embodiment of the invention will now be described with the help of the drawings, wherein.

DESCRIPTION OF THE PREFERRED EMBODIMENT

Figure 1:
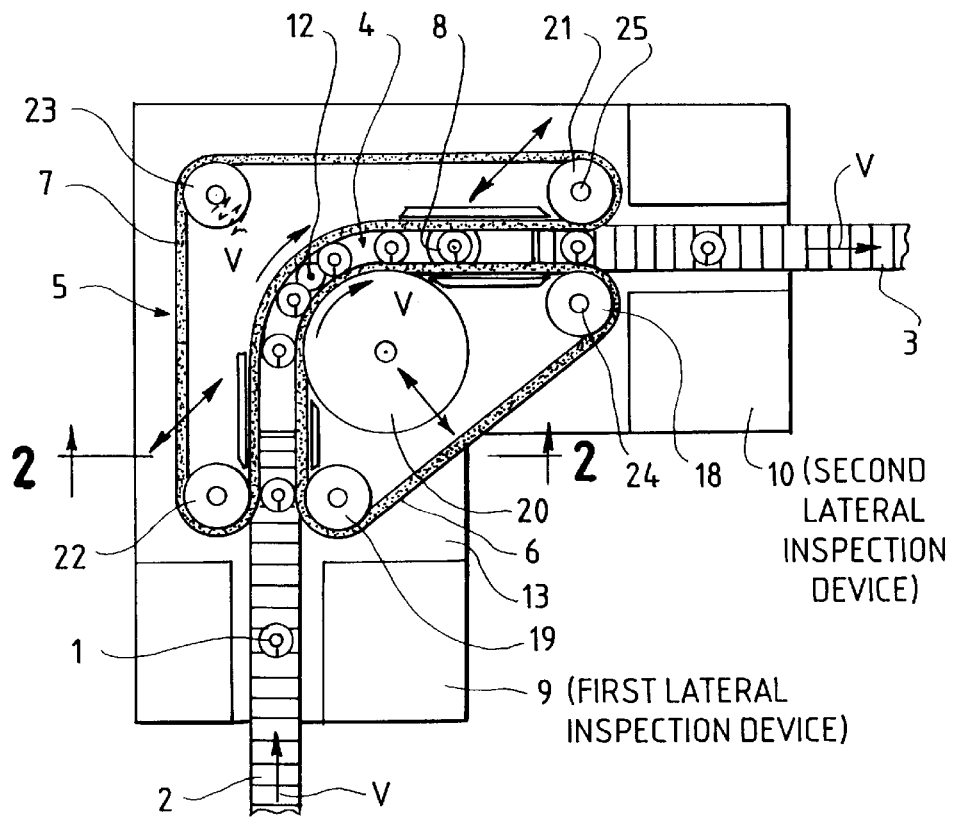
FIG. 1 shows an inspection machine in plan view.
Figure 2:
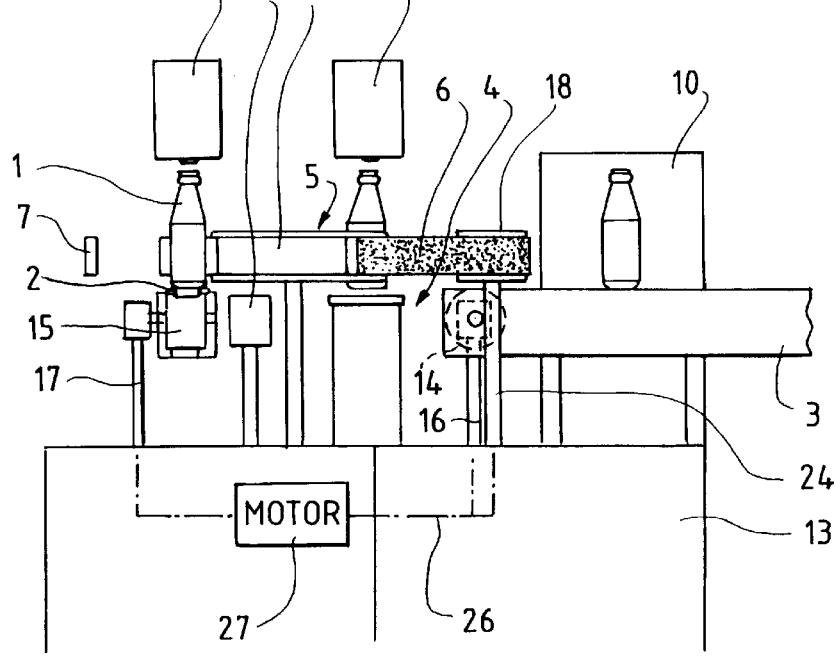
FIG. 2 shows the section A-B seen in FIG. 1.

The inspection machine as shown in FIGS. 1 and 2 is set up to check empty re-usable glass bottles with a rotationally symmetrical basic shape, referred to below as bottles 1, for dirt and foreign bodies in the area of the base and side wall and for chips in the area of the mouth. The machine incorporates a housing 13, on the upper face of which are arranged an inward conveyor 2, an outward conveyor 3 and an intermediate conveyor 5 for the bottles 1 which pass in an upright position through the inspection machine, travelling along on a path which runs in the form of a rounded right angle.

The straight inward conveyor 2 and the straight outward conveyor 3 which is arranged at a right angle thereto incorporate flat-top chains which run by means of sprocket wheels 14, 15 and are driven by driving shafts 16, 17. The flat-top chains constitute horizontal conveying surfaces, on which the bottles 1 stand and if necessary are guided by guard rails (not shown). Between the inward conveyor 2 and the outward conveyor 3 spaced apart therefrom there is a gap 4 the length of which is a multiple of the diameter of a bottle. In this gap 4 sits a blowing-off device 12 for the base of the bottle and behind it a base inspection device 8 with a light source arranged beneath the bottles 1 and a camera arranged above the bottles 1, Furthermore, a first lateral inspection device 9 having a light source and a camera is arranged on the inward conveyor 2, and a second, identical lateral inspection device 10 is arranged on the outward conveyor 3. The bottles 1 are freestanding within range of the two lateral inspection devices 9, 10 and without independently rotating on the flat-top chains of the inward conveyor 2 and outward conveyor 3, respectively, and can therefore be checked over their entire height without being disturbed. In addition, over the bottles 1 a bottle mouth inspection device 11 is provided in the region of the gap 4 above the bottles 1, immediately following the inward conveyor 2 or even above the latter.

The intermediate conveyor 5 bridges the gap 4 between the inward conveyor 2 and the outward conveyor 3 and for this purpose it sweeps the end region of the inward conveyor 2 and the initial region of the outward conveyor 3. It incorporates two endless conveyor mechanisms 6, 7, formed by toothed belts with a flexible coating of cellular rubber on the outside. The two conveyor mechanisms 6, 7 revolve in a horizontal plane at a distance from one another that is somewhat smaller than the bottle diameter, and in this way they wedge between them the bottles 1 arriving in the end region of the inward conveyor 2 once they have negotiated the first lateral inspection device 9. Next the bottles 1 are carried without support for their bases across the gap 4, or rather across the blowing-off device 12, and through the base inspection device 8, after which they are parked on the outward conveyor 3.

Each conveyor mechanism 6, 7 runs respectively over three pulleys 18 to 23, which are arranged on the corners of triangles. The pulleys 18, 21 on the outgoing side are arranged on vertical driving shafts 24, 25. These shafts are driven, by means of a gearbox 26, by a motor 27 synchronously with the inward conveyor 2 and the outward conveyor 3, in such a manner that the two conveyor mechanisms 6, 7 exhibit the same speed V and direction of travel as the inward conveyor 2 and the outward conveyor 3. The pulleys 18 to 23 are arranged in such a manner that the belt sides of the two conveyor mechanisms 6, 7, running side by side in the direction of travel, define a channel-type path for the bottles 1 in the manner of a rounded right angle. The straight section of the path on the incoming side is aligned flush with the inward conveyor 2 and the straight section on the outgoing side with the outward conveyor 3, whereas the section in the form of an arc of a circle follows the straight sections seamlessly and smoothly and is angled in an arc of 90 degrees.

As FIG. 2 shows, the mouth inspection device 11 is arranged in the first straight section, the base inspection device 8 in the second, longer straight section, and the blowing-off device 12 in the arcuate section of the path travelled by the bottles 1 in the intermediate conveyor 5. The best possible use is thus made of the path of the intermediate conveyor 5, and it is also readily possible to install additional inspection devices, e.g. for lye.

On account of the geometrical and velocity ratios outlined above, the endless conveyor mechanisms 6, 7 of the intermediate conveyor 5 transport the bottles 1 without independent rotation along two straight path sections disposed at right angles to one another and between them along an arcuate path at 90 degrees, likewise without independent bottle rotation. The spatial angular position of the bottles 1 is unaffected, as indicated by dashed marks. On account of the angular arrangement of the inward conveyor 2 and the outward conveyor 3, this results in the bottles 1 on the outward conveyor 3 appearing to be rotated through approx. 90 degrees relative to the inward conveyor 2 in terms of their translational movement. The two lateral inspection devices 9, 10 thus sweep different areas of wall of the bottles 1, which results in the desired accuracy. It will be readily understood that other angles between the inward conveyor 2 and the outward conveyor 3 with correspondingly different arcuate sections of path are also possible, which result in correspondingly greater or smaller differences in angle between the inspection ranges of the two lateral inspection devices 9, 10.

In order to make it possible to adjust the intermediate conveyor 5 to take different bottles diameters in a simple manner, the conveyor mechanism 6 including its pulleys (18 to 20) and guide rails is adjustable as a whole in the direction indicated by the double-headed arrow, whereas in the case of conveyor mechanism 7 the initial section with the pulley 22 and the corresponding guide rails, on the one hand, and the terminal section with the pulley 21 and the corresponding guide rails, on the other hand, are adapted to be adjusted separately from one another in the direction of the double-headed arrows. The pulley 23 is resiliently suspended for this purpose. In this manner, where bottles of different diameters are involved the bottles 1 keep exactly to the middle of the path, which is an advantage in terms of the inspection result. Adjustment takes place in the standard manner using slides and threaded spindles (not shown), which are arranged parallel to the double-headed arrows and are adapted to be driven synchronously. The cushioned pulley 23 in addition ensures that the conveying belt 7 is pressed flexibly against the bottles 1 in the region of the arcuate path, said bottles here taking over the guidance, as it were, of the conveying belt 7.

What is claimed is:

1. An inspection machine for bottles comprising in combination an inward conveyor, an outward conveyor, an intermediate conveyor which spans a gap between the inward and outward conveyors, at least two endless conveyor mechanisms which act on opposite sides of the bottles and are adapted to be driven at the same speed, and which transfer the bottles without rotation from said inward conveyor to said outward conveyor, a base inspection device arranged in the region of said gap, a lateral inspection device arranged in the region of said inward conveyor, said inward conveyor (2) and said outward conveyor (3) extend at an angle to one another, said intermediate conveyor (5) extends at least partially in an arc and has at least two endless transfer belts (6, 7) which act on opposite sides of the bottles and are adapted to be driven at the same speed, said transfer belts (6, 7) overlapping said inward conveyor (2) with an incoming-side section thereof and overlapping said outward conveyor (3) with an outgoing-side section thereof, a first lateral inspection device (9) is arranged on said inward conveyor (2) and a second lateral inspection device (10) is arranged on said outward conveyor.

2. Inspection machine according to claim 1, wherein said inward conveyor (2) and said outward conveyor (3) extend substantially at right angles to one another.

3. Inspection machine according to claim 2, wherein said intermediate conveyor (5) exhibits a section in the shape of an arc of approximately 90 degrees.

4. Inspection machine according to claim 3, wherein said arcuate section of said intermediate conveyor (5) is followed on opposite sides by straight sections which extend parallel to said inward conveyor (2) and said outward conveyor (3), respectively.

5. Inspection machine according to claim 4, wherein said base inspection device (8) is arranged in the straight section of said intermediate conveyor (5), which extends parallel to said outward conveyor (3).

6. Inspection machine according to claim 4 or 5, wherein a mouth inspection device (11) is disposed in the straight section of said intermediate conveyor (5), which extends parallel to said inward conveyor (2).

7. Inspection machine according to claim 3, 4 or 5, wherein a blowing-off device (12) for the base of the bottle is disposed in the arcuate section of said intermediate conveyor (5).

8. Inspection machine according to claim 1, wherein the endless transfer belts (6, 7) of intermediate conveyor (5) are adapted to be adjusted transversely or obliquely to the direction of travel.

9. Inspection machine according to claim 1, wherein each transfer belt (6, 7) revolves around at least three pulleys (18 to 22) arranged at the corners of a polygon.

* * * * *